United States Patent [19]

Broger et al.

[11] Patent Number: 5,274,125
[45] Date of Patent: Dec. 28, 1993

[54] CHIRALE PHOSPHINES

[75] Inventors: Emil A. Broger, Magden, Switzerland; Joseph Foricher, Mulhouse, France; Bernd Heiser, Inzlingen, Fed. Rep. of Germany; Rudolf Schmid, Arlesheim, Switzerland

[73] Assignee: Hoffmann-La Roche Inc., Nutley, N.J.

[21] Appl. No.: 949,871

[22] PCT Filed: Mar. 11, 1992

[86] PCT No.: PCT/CH92/00049
§ 371 Date: Nov. 13, 1992
§ 102(e) Date: Nov. 13, 1992

[87] PCT Pub. No.: WO92/16536
PCT Pub. Date: Oct. 1, 1992

[30] Foreign Application Priority Data

Mar. 15, 1991 [CH]  Switzerland ............... 805/91
Mar. 5, 1992 [CH]  Switzerland ............... 697/92

[51] Int. Cl.$^5$ .............. C07D 307/34; C07D 333/04; C07F 9/28; C07F 9/547
[52] U.S. Cl. ...................... 549/216; 549/6; 548/412
[58] Field of Search ............. 549/216, 6; 548/412

[56] References Cited

U.S. PATENT DOCUMENTS 4,556,740  12/1985  Hansen et al. ............... 568/13
4,634,775  1/1987  Beck et al. ............... 548/402

FOREIGN PATENT DOCUMENTS 104375  8/1983  European Pat. Off. .
151282  12/1984  European Pat. Off. .
198696  4/1986  European Pat. Off. .
305012  8/1988  European Pat. Off. .
398132  5/1990  European Pat. Off. .

OTHER PUBLICATIONS

C. K. Mirabelli, et al., *J. Med. Chem.*, 30:2181-90, (1987).

*Primary Examiner*—Marianne M. Cintins
*Assistant Examiner*—Margaret J. Page
*Attorney, Agent, or Firm*—George M. Gould; William H. Epstein

[57] ABSTRACT

Novel, racemic and optically active phosphorus compounds of the formula

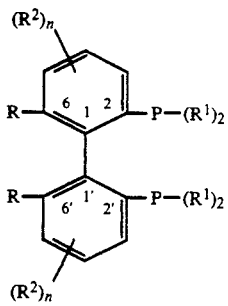

wherein R signifies lower alkyl, lower alkoxy or a protected hydroxy group, $R^1$ signifies a five membered heteroaromatic ring, $R^2$ stands for lower alkyl or lower alkoxy and n represents the number 0, 1 or 2, are described. The compounds of formula I serve in the form of complexes with a metal of Group VIII as catalyst for asymmetric hydrogenations and for enantioselective hydrogen displacements in prochiral allylic systems.

8 Claims, No Drawings

CHIRALE PHOSPHINES

The present invention is concerned with novel, racemic and optically active phosphorus compounds of the general formula

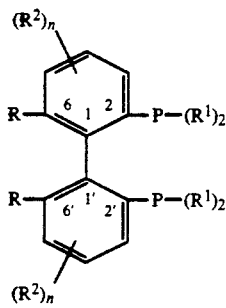

wherein R signifies lower alkyl, lower alkoxy or a protected hydroxy group, $R^1$ signifies a five-membered heteroaromatic ring, $R^2$ stands for lower alkyl or lower alkoxy and n represents the number 0, 1 or 2.

The invention is also concerned with the manufacture of the phosphorus compounds of formula I as well as their use for enantioselective reactions such as e.g. asymmetric hydrogenations or enantioselective hydrogen displacements in prochiral allylic systems.

The term "lower alkyl" signifies in the scope of the present invention straight-chain or branched alkyl groups with 1 to 4 carbon atoms such as methyl, ethyl, propyl, isopropyl, n-butyl, isobutyl and tert.butyl. The term "lower alkoxy" signifies groups in which the alkyl residue has the foregoing significance. As protecting groups for the hydroxy group there come into consideration in the scope of the present invention especially the usual ether-forming groups such as e.g. benzyl, allyl, benzyloxymethyl, lower alkoxymethyl, 2-methoxyethoxymethyl and the like. The term "five-membered heteroaromatic ring" stands in the scope of the present invention for a substituent of the formula

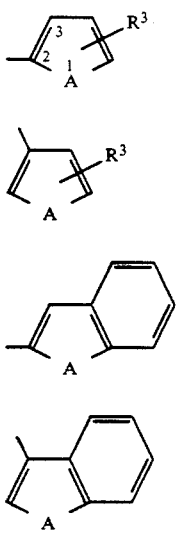

In the substituents of formulae (a) to (d) A signifies oxygen, sulphur or $-NR^4$. The substituent $R^3$ signifies hydrogen, lower alkyl, especially methyl, or lower alkoxy, especially methoxy, and $R^4$ stands for lower alkyl, preferably methyl.

The phosphorus compounds of formula I can be present not only in racemic form, but also in optically active form. Preferred compounds of formula I are those in which n stands for the number 0 and R signifies methoxy, methoxymethyl or methyl. Further, those in which $R^1$ represents 2- or 3-furyl or 2-thienyl are also preferred. Especially preferred compounds of formula I are:

(RS)-(6,6'-Dimethoxybiphenyl-2,2'-diyl)bis(di-2-furylphosphine), (R)- or (S)-(6,6'-dimethoxybiphenyl-2,2'-diyl)bis(di-2-furylphosphine), (RS)-(6,6'-dimethoxybiphenyl-2,2'-diyl)bis(di-2-thienylphosphine), (R)- or (S)-(6,6'-dimethoxybiphenyl-2,2'-diyl)bis(di-2-thienylphosphine), (RS)-(6,6'-dimethoxybiphenyl-2,2'-diyl)bis(di-3-furylphosphine), (R)- or (S)-(6,6'-dimethoxybiphenyl-2,2'-diyl)bis(di-3-furylphosphine), (RS)-(6,6'-dimethylbiphenyl-2,2'-diyl)bis(di-2-furylphosphine), (R)- or (S)-(6,6'-dimethylbiphenyl-2,2'-diyl)bis(di-2-furylphosphine), (RS)-(6,6'-dimethylbiphenyl-2,2'-diyl)bis(di-2-thienylphosphine), (R)- or (S)-(6,6'-dimethylbiphenyl-2,2'-diyl)bis(di-2-thienylphosphine), (RS)-[6,6'-bis(methoxymethoxy)biphenyl-2,2'-diyl]bis(di-2-furylphosphine), (R)- or (S)-[6,6'-bis(methoxymethoxy)biphenyl-2,2'-diyl]bis(di-2-furylphosphine), (RS)-[6,6'-bis(methoxymethoxy)biphenyl-2,2'-diyl]bis(di-2-thienylphosphine), (R)- or (S)-[6,6'-bis(methoxymethoxy)biphenyl-2,2'-diyl]bis(di-2-thienylphosphine)

(RS)-(6,6'-dimethoxybiphenyl-2,2'-diyl)bis[bis(5-methylfuran-2-yl)phosphine, (R) or (S)-(6,6'-dimethoxybiphenyl-2,2'-diyl)bis[bis(5-methylfuran-2-yl)phosphine, (RS)-(6,6'-dimethoxybiphenyl-2,2'-diyl)bis[di-(2-benzo[b]furanyl)phosphine].

(R)- or (S)-(6,6'-dimethoxybiphenyl-2,2'-diyl)bis[di-(2-benzo[b]furanyl)phosphine].

(RS)-(6,6'-Dimethoxybiphenyl-2,2'-diyl)bis(dibenzo[b]thiophen-2-yl)phosphine, (R)- or (S)-(6,6'-dimethoxybiphenyl-2,2'-diyl)bis-(dibenzo[b]thiophen-2-yl)phosphine, (RS)-(6,6'-dimethoxybiphenyl-2,2'-diyl)bis[bis(1-methyl-pyrrol-2-yl)phosphine], (R)- or (S)-(6,6'-dimethoxybiphenyl-2,2'-diyl)bis[bis(1-methylpyrrol-2-yl)phosphine].

The compounds of formula I in accordance with the invention can be manufactured e.g. by reacting a racemic or optically active compound of the general formula

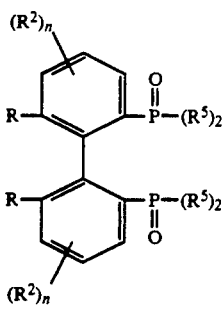

wherein R, $R^2$ and n have the above significance and $R^5$ signifies lower alkoxy, phenoxy, benzyloxy, chlorine or bromine, with a compound of the formula $$R^1MgX \text{ or } R^1Li$$

wherein $R^1$ has the above significance and X represents chlorine, bromine or iodine, to give a compound of the formula

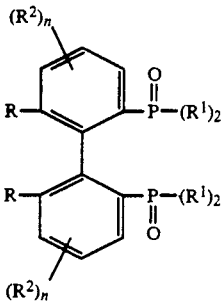

wherein R, $R^1$, $R^2$ and n have the above significance, and reducing this, if desired after resolution into the (R) form and (S) form using O,O'-dibenzoyltartaric acid or O,O'-di-p-toluyltartaric acid, to a compound of formula I.

The reaction of a compound of formula II with $R^1MgX$ or $R^1Li$ can be effected in a manner known per se. This is preferably effected e.g. under the usual conditions of a Grignard reaction.

The reduction of a racemic compound of formula III or of a compound of formula III which is present in the (R) or (S) form can be carried out in a manner known per se. This can be effected, for example, with silanes such as e.g. trichlorosilane in an aromatic hydrocarbon such as, for example, in boiling xylene or in acetonitrile etc., conveniently in the presence of an auxiliary base such as, for example, triethylamine or preferably tributyl- amine. If desired, this reduction can also be carried out in an autoclave under pressure.

The compounds of formula II which are used as starting materials can be prepared, for example, by subjecting a compound of the formula

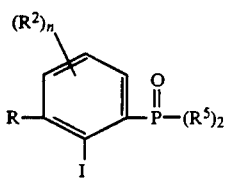

wherein R, $R^2$ and n have the above significance and $R^5$ also has the above significance with the exception of chlorine or bromine, to an Ullmann coupling and if desired, resolving a thus-obtained compound of the formula

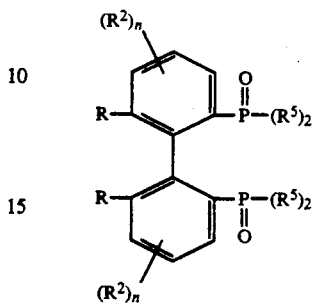

wherein R, $R^2$, $R^5$ and n have the significance from formula IV, which is present in the (RS) form into the (R) form and (S) form using O,O'-dibenzoyltartaric acid or O,O'-di-p-toluyltartaric acid and, if desired, replacing a lower alkoxy group denoted by $R^5$ in a racemic or optically active compound of formula II by chlorine or bromine.

The conversion of a compound of formula IV into a compound of formula II which is present in the (RS) form is effected by means of an Ullmann coupling. This is a reaction which is known per se and which can be carried out under the conditions which are usual for this. Thus, this reaction can be carried out, for example, by heating a compound of formula IV in an inert organic solvent such as e.g. N,N-dimethylformamide with e.g. copper powder activated with iodine to a temperature of about 110° C. to about 200° C. If desired, the reaction can also be carried out in the absence of a solvent, i.e. in the melt.

The compounds of general formula IV which are used as starting materials can be prepared when R is different from lower alkyl by, for example, subjecting a compound of the general formula

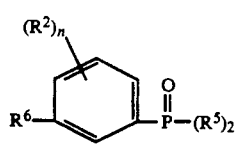

wherein $R^2$, $R^5$ and n have the significance from formula IV and $R^6$ signifies lower alkoxy or protected hydroxy, to an otho-lithiation/iodination reaction.

The ortho-lithiation of a compound of formula V can be effected in a manner known per se. For example, this reaction can be effected by reacting a compound of formula V with a lithium amide, e.g. lithium diisopropylamide or lithium 2,2,6,6-tetramethylpiperidine, in tetrahydrofuran at a temperature below 0° C., preferably at about −50° C. to about −78° C. The subsequent iodination can be effected conveniently with molecular iodine, with ICl or IBr, likewise in tetrahydrofuran and likewise at a temperature below −50° C.

Those starting materials of formula IV in which R signifies lower alkyl can be prepared, for example, starting from a compound of the formula

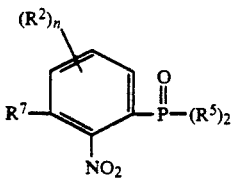

wherein $R^2$, $R^5$ and n have the significance from formula IV and $R^7$ represents lower alkyl.

This is conveniently effected by the generally known reduction of the nitro group to the amino group, e.g. by means of hydrogen in the presence of a catalyst such as, for example, Pd/C, and subsequent diazotization/iodination in a manner known per se.

The compounds of formulae V and VI which are also used as starting materials are known compounds or are analogues of known compounds which can be prepared readily in a manner known per se; compounds V e.g. in accordance with J. J. Monagle et al., J. Org. Chem. 32, 2477 (1967) and compounds VI e.g. in accordance with K. S. Petrakis et al., J. Am. Chem. Soc. 1987, 109, 2831.

Alternatively, those compounds of formula II in which R represents lower alkyl and $R^5$ is different from chlorine or bromine can also be obtained starting from compounds of the formula

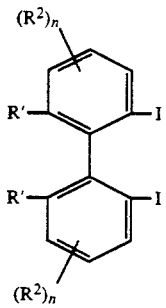

wherein $R^2$ and n have the above significance and R' represents lower alkyl.

This can be effected in a manner which is simple and known per se, e.g. by reacting a compound of formula VII with a compound of the formula

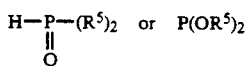

wherein $R^5$ has the above significance with the exception of chlorine or bromine, in the presence of a tert. amine such as, for example, triethylamine and a catalyst such as e.g. Pd(P(phenyl)$_3$)$_4$ or in the presence of a catalyst such as e.g. PdCl$_2$ or NiCl$_2$.

The racemate resolution of a compound of formula II (wherein $R^5$ is different from chlorine or bromine) or III, which is present in the (RS) form, by means of (−)- or (+)-O,O′-dibenzoyltartaric acid (DBT) or (−)- or (+)-O,O′-di-p-toluyltartaric acid (DTT) can be carried out in an analogous manner to the racemate resolution of phosphine oxides, although this actually was unexpected for the compounds of formula II having regard to the state of the art. This is conveniently effected in an inert organic solvent and at a temperature of about 0° C. to about 60° C. As solvents there can be mentioned here especially chloroform, methylene chloride, ethyl acetate, isopropyl acetate, acetone, alcohols such as methanol or ethanol and the like, as well as mixtures thereof.

The thus-obtained adducts of the compounds of formula II or III with (−)- or (+)-DBT or DTT can subsequently be treated with an inorganic base in an analogous manner to phosphine oxide adducts, whereby the respective (R) or (S) form of the compounds of formula II or III is liberated.

When $R^5$ signifies lower alkoxy in a racemic or optically active compound of formula II, this can be replaced by chlorine or bromine. This substitution can be effected in a manner known per se, for example by reaction with thionyl chloride, thionyl bromide or phosphorus pentachloride in an inert organic solvent.

All previously mentioned reactions—with the exception of the racemate resolution—are conveniently carried out under an inert gas such as e.g. argon or nitrogen.

The phosphorus compounds of formula I in accordance with the invention form complexes with transition metals such as, for example, metals of Group VIII, especially with ruthenium, rhodium and iridium, which can be used as catalysts in asymmetric hydrogenations and for enantioselective hydrogen displacements in prochiral allylic systems. Ruthenium and rhodium complexes are preferred for the aforementioned hydrogenations, while rhodium complexes are preferred for isomerizations. These catalysts, i.e. a complex of a metal of Group VIII and the phosphorus compounds of formula I, are novel and are likewise an object of the present invention.

The complexes in question can be manufactured in manner known per se, e.g. by reacting a compound of formula I with a compound which can yield a metal of Group VIII in a suitable inert organic or aqueous solvent. As suitable compounds which yield e.g. rhodium there can be mentioned, for example, organic rhodium complexes with ethylene, propylene and the like and with bis-olefins, e.g. (Z,Z)-1,5-cyclooctadiene, 1,5-hexadiene, bicyclo- [2.2.1]hepta-2,5-diene or with other dienes which form readily soluble complexes with rhodium. Preferred compounds which yield rhodium are e.g. di-μ-chloro-bis[η$^4$-(Z,Z)-1,5-cyclooctadiene]dirhodium(I), di-μ-chloro-bis[η$^4$-norbornadiene]dirhodium(I), bis[η$^4$-(Z,Z)-1,5-cyclooctadiene]rhodium tetrafluoroborate or bis[η$^4$-(Z,Z)-cyclooctadiene]rhodium perchlorate. Di-η-chloro-bis[η$^4$-(Z,Z)-1,5-cyclooctadiene]diriridium(I) can be named, for example, as a compound which yields iridum.

The ruthenium complexes in question can be represented e.g. by the following formula

wherein Z represents halogen or the group A-COO, A represents lower alkyl, aryl, halogenated lower alkyl or halogenated aryl and L represents a chiral diphosphine ligand of formula I.

These complexes can in principle be manufactured in a manner known per se. Conveniently and preferably, ruthenium complexes are manufactured, for example, by reacting a complex of the formula

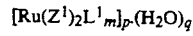

wherein $Z^1$ represents halogen or a group $A^1$-COO, $A^1$ represents lower alkyl or halogenated lower alkyl, $L^1$ represents a neutral ligand, m represents the number 1, 2 or 3, p represents the number 1 or 2 and q represents the number 0 or 1, with a chiral diphosphine ligand of formula I, or by reacting a ruthenium complex of the formula

wherein L represents a chiral diphosphine ligand of formula I, with a salt yielding the anion Z, wherein Z has the above significance.

The term "neutral ligand" signifies in the scope of the present invention a readily exchangeable ligand such as, for example, a diolefin, e.g. norbornadiene, (Z,Z)-1,5-cyclooctadiene etc., or a nitrile such as acetonitrile, benzonitrile and the like. Where m represents the number 2 or 3, the ligands can be the same or different.

The ruthenium complexes of formula IX are known substances or are analogues of known substances which can be obtained readily in an analogous manner to the preparation of the known substances, for example in accordance with Albers, M. O. et al., Organomet. Chem. 272, C62-C66 (1984).

The reaction of a ruthenium complex of formula IX with a chiral diphosphine ligand of formula I can be carried out in a manner known per se. This reaction can be conveniently effected in an inert organic solvent. As examples of such solvents there can be named e.g. ethers such as tetrahydrofuran or dioxan, ketones such as, for example, acetone, lower alcohols such as, for example, methanol, ethanol etc., halogenated hydrocarbons such as methylene chloride, chloroform and the like, or mixtures of such solvents. Moreover, the reaction can be effected at a temperature between about 0° C. and about 100° C., preferably between about 15° C. and about 60° C., but with the strict exclusion of oxygen.

The reaction of a ruthenium complex of formula X (obtainable from a complex of formula IX) with a salt containing the anion Z can be effected in a manner known per se. The term "a salt yielding the anion Z" signifies in the scope of the present invention, for example, ammonium salts, alkali metal salts or other suitable metal salts. In order to improve the solubility of such salts, crown ethers or the like can be added in certain instances.

As mentioned earlier, the phosphorus compounds in accordance with the invention in the form of complexes with metals of Group VIII, especially ruthenium, can be used, inter alia, for asymmetric hydrogenations. As particularly suitable substrates there can be mentioned in this connection allyl alcohols such as e.g. geraniol, 6,7-dihydrogeraniol, 6,7-dihydrofarnesol, 6,7,10,11-tetrahydrofarnesol and the like, as well as β-ketoesters such as e.g. methyl or ethyl acetoacetate etc.

In carrying out such hydrogenations, these complexes can firstly be prepared and then added to a solution of the substance to be hydrogenated. Alternatively, however, they can also be produced in situ, e.g. in the presence of the substance to be hydrogenated.

The asymmetric hydrogenation can be effected in a suitable organic solvent which is inert under the reaction conditions. As such solvents there can be named, in particular, lower alcohols such as e.g. methanol or ethanol or mixtures of such alcohols with halogenated hydrocarbons such as methylene chloride, chloroform and the like or with cyclic ethers such as tetrahydrofuran or dioxan, and the like.

The ratio of ruthenium to the ligand L conveniently lies between about 0.5 and about 2 mol, preferably at about 1 mol, of ruthenium per mol of ligand. The ratio of ruthenium in the complexes of formula VIII to the substances to be hydrogenated conveniently lies between about 0.0005 and about 1 mol %, preferably between about 0.002 and about 0.1 mol %.

The asymmetric hydrogenation with the complexes of formula VIII is conveniently effected at a temperature of about 0° C. to about 100° C. depending on the substrate which is used. This hydrogenation is also conveniently effected under pressure, preferably at a pressure of about 5 to about 200 bar, particularly of about 30 to about 100 bar.

Furthermore, as mentioned earlier, the aforementioned catalysts are useful for enantioselective hydrogen displacements in prochiral allylic systems. They are especially interesting e.g. in connection with the manufacture of optically active compounds of the general formula

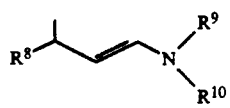

wherein $R^8$ represents protected hydroxymethyl or a residue of the formula

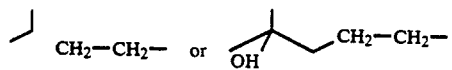

wherein the dotted line can represent an additional bond and $R^9$ and $R^{10}$ signify lower alkyl (1-7 C atoms), starting from compounds of the general formula

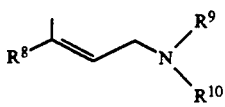

wherein $R^8$, $R^9$ and $R^{10}$ have the above significance.

The compounds XI and, respectively, the aldehydes obtained therefrom by hydrolysis as well as the acids and alcohols derived from the latter are e.g. of interest as intermediates in the synthesis of the side-chains of vitamins E and $K_1$.

In order to carry out the aforementioned hydrogen displacements, the phosphorus compounds of formula I can be brought into contact as such, in a solution of a compound to be treated, with a compound yielding e.g. rhodium or iridium. Alternatively, the phosphorus compounds of formula I can firstly be converted in a suitable solvent with a compound yielding e.g. rhodium or iridium into the corresponding catalyst complex and this can then be added to a solution of a compound to be treated. The latter method is preferred.

Not only the reaction of the phosphorus compounds of formula I with a compound yielding e.g. rhodium or iridium, but also the aforementioned hydrogen displacements can be carried out in suitable organic solvents which are inert under the reaction conditions. As such there can be mentioned especially lower alkanols such as e.g. methanol or ethanol, aromatic hydrocarbons such as benzene or toluene, cyclic ethers such as tetrahydrofuran or dioxan, esters such as e.g. ethyl acetate or mixtures thereof, and the like. Furthermore, the complex formation can also be carried out in aqueous medium or in dichloromethane.

The ratio between e.g. rhodium or iridium and the ligands of formula I conveniently lies between about 0.05 and about 5 mol, preferably between about 0.5 and about 2 mol, of metal per mol of ligand of formula I.

The amount of metal in the complexes with the ligands of formula I based on the compounds to be treated conveniently lies between about 0.005 and about 0.5 mol %, preferably between about 0.01 and about 0.2 mol %.

The aforementioned hydrogen displacements using metal complexes with the ligands of formula I can be carried out conveniently in an inert organic solvent and at a temperature from about room temperature to about 130° C. This reaction is preferably effected at an elevated temperature, i.e. depending on the solvent used either at the reflux temperature of the reaction mixture or in a sealed vessel under pressure.

In analogy to the manufacture and use of the compounds of formula I, compounds of the binaphthyl type of the following formula

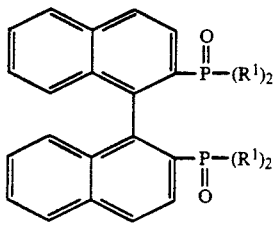

XIII wherein $R^1$ has the above significance, can likewise be manufactured and used. The binaphthyl rings can be substituted in the usual manner.

The following Examples serve to illustrate the invention and in no manner represent any limitation. In these Examples the selected abbreviations have the following significance:

TLC: thin layer chromatography
DBT: O,O'-dibenzoyltartaric acid
THF: tetrahydrofuran
RT: room temperature All temperatures are given in °Celsius.

EXAMPLE 1 a) A solution of 0.30 g (0.442 mmol) of (R)-(6,6'dimethoxybiphenyl-2,2'-diyl)bis(phosphonic acid diphenyl ester) in 10 ml of tetrahydrofuran was added dropwise within 15 minutes at room temperature to a Grignard solution prepared from 1.5 ml of 2-iodofuran (67% pure) and 0.30 g (12.3 mmol) of magnesium turnings in 10 ml of tetrahydrofuran. After completion of the addition the mixture was heated at 40° for 1 hour. For the working-up, the mixture was treated with 50 ml of sat. NH$_4$Cl solution and 50 ml of ethyl acetate, the phases were separated and the organic phase was washed with sat. NaCl solution, dried over M$_g$SO$_4$, filtered and concentrated. The residue was dissolved in the minimum amount of CH$_2$Cl$_2$ and the solution was placed on a column of 50 g of silica gel. Elution with ethyl acetate and then with tetrahydrofuran yielded 0.20 g of a solid which was recrystallized from 10 ml of tert. butyl methyl ether. There was obtained 0.16 g of (R)-(6,6'-dimethoxybiphenyl-2,2'-diyl)bis(di-2-furylphosphine oxide) as yellowish crystals, m.p. 272° (thermoanalysis); $[\alpha]_D^{20} = +89.6$ (c=1.0, CHCl$_3$).

b) A 0.5 l four-necked flask provided with a condenser, thermometer, dropping funnel and mechanical stirrer was charged under argon with 2.90 g (5.0 mmol) of (R)-(6,6'-dimethoxybiphenyl-2,2'-diyl)bis(di-2-furylphosphine oxide), 10 ml (41.9 mmol) of tributylamine, 60 ml of xylene isomer mixture and 4.0 ml (5.37 g, 39.6 mmol) of trichlorosilane. The milky-white mixture was boiled under reflux for 4 hours, whereby an almost translucent solution resulted. After cooling 100 ml of deoxygenated 30% sodium hydroxide solution were added dropwise while stirring well in such a manner that the internal temper-ature did not exceed 70° and the mixture was stirred at 70° for a further 1 hour. After the addition of H$_2$O and CH$_2$Cl$_2$ the phases were separated and the organic phase was washed with 2×50 ml of 30% sodium hydroxide solution, H$_2$O, sat. NH$_4$Cl solution and sat. NaCl solution, dried over MgSO$_4$, filtered and evaporated. The white powder obtained (4.40 g) was dissolved in CH$_2$Cl$_2$, the solution was treated with ethanol and the CH$_2$Cl$_2$ was evaporated on a rotary evaporator. The precipitated solid was filtered off, washed with ethanol and pentane and dried in a high vacuum (~10 Pa) for 1 hour at 100°. There were obtained 2.50 g of (R)-(6,6'dimethoxybiphenyl-2,2'-diyl)-bis(di-2-furylphosphine) as yellowish crystals; m.p. 176°; $[\alpha]_D^{20} = +6.9$ (c=1, CHCl$_3$).

The following compounds were prepared in an analogous manner to the foregoing:

(S)-(6,6'-Dimethoxybiphenyl-2,2'-diyl)bis(di2-furylphosphine oxide). M.p. 270° (thermoanalysis). $[\alpha]_D^{20} = -87.9$ (c=1, CHCl$_3$).

(S)-(6,6'-Dimethoxybiphenyl-2,2'-diyl)bis(di-2-furylphosphine). M.p. 175° (thermoanalysis). $[\alpha]_D^{20} = -7.6$ (c=1, CHCl$_3$).

The (R)-(6,6'-dimethoxybiphenyl-2,2'-diyl)bis(phosphonic acid diphenyl ester) used as the starting material and, respectively, the corresponding (S) compound were prepared as follows:

a) 76.5 g (0.122 mol) of (2-iodo-3-methoxyphenyl)-phosphonic acid diphenyl ester (75% pure) and 25.0 g (0.393 mol) of activated copper powder were placed under argon in a 1 l four-necked sulphonation flask provided with a condenser, thermometer, stirrer and headpiece for inert gas treatment and 200 ml of N,N-dimethylformamide were allowed to flow in. The dark brown suspension was heated at 140° (oil bath temperature) for 1 hour, after which time complete conversion had taken place according to TLC analysis. The cooled reaction mixture was transferred into a round flask with methylene chloride and evaporated to dryness at 70° on a rotary evaporator. The residue was treated with 200 ml of methylene chloride, the mixture was stirred well and filtered and the filter residue was washed with 100 ml of methylene chloride. The filtrate was washed three times with 100 ml of sat. NH$_4$Cl solution, whereby a small amount of solid formed was filtered off in the first wash operation, and subsequently dried over MgSO$_4$, filtered and concentrated. After drying in a high vacuum (~10 Pa) for 2 hours at 80° there were obtained 59.6 g of crude (RS)-(6,6'-dimethoxybiphenyl-2,2'-diyl)-bis(phosphonic acid diphenyl ester).

ba) A solution of 59.6 g of the crude diphenyl ester obtained in accordance with a) in 50 ml of dichloromethane was placed in a 1 l round flask and treated with a solution of 35.8 g (0.10 mol) of (—)-O,O'-dibenzoyl-L-tartaric acid in 100 ml of ethyl acetate. The solution was then evaporated on a rotary evaporator at 600 mbar, whereby the CH$_2$Cl$_2$ distilled off and a white solid separated. This was filtered off under suction, washed three times with 20 ml of ethyl acetate and 20 ml of hexane and dried in a high vacuum (~10 Pa). There were obtained 21.8 g of (R)-diphenyl ester/(−)-DBT adduct as a white powder. $[\alpha]_D^{20} = -95.6$ (c=1 in ethanol).

The mother liquors and wash solutions were placed on one side in order to obtain the other enantiomer.

bb) The material obtained in accordance with ba) was triturated with 100 ml of dichloromethane, 50 ml of sat. NaHCO$_3$ solution and 50 ml of deionized water in a 1 l Erlenmeyer having a magnetic stirrer until all of the solid had passed into solution (30 minutes). The phases were separated and the organic phase was washed twice with 100 ml of semi-sat. NaHCO$_3$ solution, 50 ml of deionized water and 50 ml of sat. NaCl solution, dried over MgSO$_4$, filtered and evaporated. The oily residue was treated with 20 ml of tert.-butyl methyl ether, whereby crystallization set in. After evaporation and drying in a high vacuum (~10 Pa) for 1 hour at 60° there were obtained 13.8 g of (R)-(6,6'-dimethoxybiphenyl-2,2'-diyl)bis(phosphonic acid diphenyl ester) as white crystals. M.p. 125°–125.5°; $[\alpha]_D^{20} = -18.9$ (c=1 in CHCl$_3$).

ca) The mother liquors and wash solutions from ba) were evaporated in a 1 l round flask. The residue was taken up in 100 ml of dichloromethane and the solution was triturated for 30 minutes with 50 ml of sat. NaHCO$_3$ solution and 50 ml of deionized water. The phases were separated and the organic phase was washed with 100 ml of semi-sat. NaHCO$_3$ solution, 50 ml of deionized water and 50 ml of sat. NaCl solution, dried over MgSO$_4$, filtered and concentrated. The brown oil obtained was taken up in 50 ml of dichloromethane and the solution was treated with a solution of 18.0 g (0.050 mol) of (+)-O,O'-dibenzoyl-D-tartaric acid in 100 ml of ethyl acetate. The solution was then concentrated on a rotary evaporator at 600 mbar, whereby the CH$_2$Cl$_2$ distilled off and white solid separated. This was filtered off under suction, washed three times with 20 ml of ethyl acetate and 20 ml of hexane and dried in a high vacuum (~10 Pa). There were obtained 22 g of (S)-diphenyl ester/(+)-DBT adduct as a light yellowish powder. $[\alpha]_D^{20} = +96$ (c=1 in ethanol).

cb) The material obtained in accordance with ca) was worked-up as described in bb). There were obtained 13.9 g of (S)-(6,6'-dimethoxybiphenyl-2,2'-diyl)bis(phosphonic acid diphenyl ester) as white crystals. M.p. 124°–125°; $[\alpha]_D^{20} = +18.7$ (c=1 in CHCl$_3$).

d) The (2-iodo-3-methoxyphenyl)phosphonic acid diphenyl ester used as the starting material was prepared as follows:

daa) A suspension of 13.0 g (0.535 mol) of magnesium shavings in 50 ml of dry tetrahydrofuran was placed under argon in a 0.51 l four-necked flask provided with a stirrer, condenser, thermo- meter and headpiece for inert gas treatment. Thereto there was added dropwise within 90 minutes a solution of 93.5 g (0.50 mol) of 3-bromoanisole in 200 ml of dry tetrahydrofuran in such a manner that the reaction temperature did not exceed 35°. After the addition the mixture was diluted with an additional 150 ml of dry tetrahydrofuran in order to prevent the precipitation of the Grignard reagent.

dab) 259.8 g (0.967 mol) of diphenyl chlorophosphate and 200 ml of dry tetrahydrofuran were placed in a 1.5 l four-necked flask provided with a stirrer, thermometer, headpiece for inert gas treatment and CO$_2$/acetone cooling bath and the solution was cooled to −78°. Thereto there was now added dropwise the solution of the Grignard reagent prepared in accordance with baa) in such a manner that the reaction temperature did not exceed −70°. After completion of the addition the mixture was left to warm to room temperature overnight while stirring. The reaction mixture, which contained some fine white precipitate, was poured into a mixture of 2 l of ice-water, 2 l of sat. NaHCO$_3$ solution and 1 l of diethyl ether in a 10 l stirring vessel. After vigorous stirring for 10 minutes the aqueous phase was separated and the organic phase was washed in succession with 1 l of sat. NaHCO$_3$ solution, 200 ml of 25% ammonia, 100 ml of 25% ammonia and three times with 500 ml of sat. NaCl solution. After drying over MgSO$_4$ the solution was evaporated, the residue was taken up in 1 l of diethyl ether and the solution was left to stand at 0° overnight. The white solid (12 g) which thereby separated was removed by filtration and discarded. The filtrate was evaporated, dried in a high vacuum (~10 Pa), the residue obtained (163 g of yellow oil) was taken up in 300 ml of hexane/toluene 1:1 and the solution was filtered over 500 g of silica gel. By elution firstly with 3 l of hexane and 8 l of hexane/ethyl acetate 9:1 and thereafter with 2 l of hexane/ethyl acetate 4:1 and 2 l of hexane/ethyl acetate 7:3 there were obtained, after drying in a high vacuum (~10 Pa) for 1 hour at 40°, 118 g of (3-methoxyphenyl)phosphonic acid diphenyl ester as a slightly yellowish oil.

db) 300 ml of dry tetrahydrofuran were placed in a 1.5 l four-necked flask provided with a stirrer, thermometer, headpiece for inert gas treatment, dropping funnel with pressure balance and CO$_2$/acetone cooling bath. 70 ml (0.412 mol) of 2,2,6,6-tetramethylpiperidine were added thereto using a syringe and the solution was cooled to −78°. 210 ml (0.336 mol) of 1.6N butyllithium solution in hexane were filled into the dropping funnel via a steel canula. The butyllithium solution was dropped into the reaction vessel within about 10 minutes, whereby the temperature rose to about −50° and a white precipitate formed. The CO$_2$/acetone cooling bath was replaced by an ice/ethanol bath and the reaction mixture was stirred at about −15° for a further 30 minutes, then again cooled to −78°.

250 ml of dry tetrahydrofuran and 95.2 g (0.280 mol) of (3-methoxyphenyl)phosphonic acid diphenyl ester (material from dab) were placed under argon in a separate 1 l round flask and the solution was cooled to −78°. This solution was now allowed to flow via a steel canula into the above reaction mixture within about 10 minutes, whereby the temperature rose to about −68° and a translucent, caramel-coloured solution resulted. This was stirred at −78° for a further 30 minutes.

A solution of 71.06 g (0.280 mol) of iodine in 150 ml of dry tetrahydrofuran was prepared under argon in a separate 250 ml Schlenk tube and the solution was transferred via a steel canula into the dropping funnel of the reaction apparatus. The reaction mixture was now titrated within 15 minutes by the rapid dropwise addition of the iodine solution, whereby the reaction temperature rose to −65°. After the dropwise addition of about 145 ml of the about 170 ml of iodine solution, when a red coloration of the reaction mixture remained, the addition was interrupted and the mixture was left to warm to 0°. Then, the reaction mixture was treated with 150 ml of a solution of 100 g of sodium thiosulphate pentahydrate in 200 ml of deionized water, stirrer vigorously and subsequently treated with 100 ml of sat.

NaHCO₃ solution. The two-phase system was filtered in order to remove the precipitate formed and the phases were separated. The aqueous phase was re-extracted once with 250 ml of ethyl acetate and the combined organic phases were washed with 250 ml of sat. NaCl solution, dried over MgSO₄ and evaporated. The residue was taken up in 500 ml of ethyl acetate and the solution was washed three times with 250 ml of deionized water and with 250 ml of sat. NaCl solution, dried over MgSO₄, filtered and concentrated. The residue (118 g of yellow oil) was taken up in 170 ml of toluene and the solution was treated with 115 ml of hexane, whereby a white precipitate separated. This was removed by filtration and the filtrate was applied to a column of 450 g of silica gel. Byproducts were firstly eluted with 2 l of hexane/ethyl acetate 9:1 and 3 l of hexane/ethyl acetate 8:2. Subsequently, fractions containing the end product were eluted with 2 l of hexane/ethyl acetate 7:3. After evaporation and drying in a high vacuum (∼10 Pa) for 1 hour at 60° there were obtained 76.5 g of an orange oil. This consisted in accordance with ¹H-NMR analysis of 75 mol % of (2-iodo-3-methoxyphenyl)phosphonic acid diphenyl ester.

EXAMPLE 2

The following compounds were prepared in an analogous manner to Example 1:

(R)-(6,6'-Dimethoxybiphenyl-2,2'-diyl)bis(di-2-thienylphosphine oxide). M.p. 337° (thermoanalysis). $[\alpha]_D^{20} = +141.3$ (c=1, CHCl₃).

(R)-(6,6'-Dimethoxybiphenyl-2,2'-diyl)bis(di-2-thienylphosphine). M.p. 230° (thermoanalysis). $[\alpha]_D^{20} = +147.5$ (c=1, CHCl₃).

(S)-(6,6'-Dimethoxybiphenyl-2,2'-diyl)bis(di-2-thienylphosphine oxide). M.p. 338° (thermoanalysis). $[\alpha]_D^{20} = -140.7$ (c=1, CHCl₃).

(S)-(6,6'-Dimethoxybiphenyl-2,2'-diyl)bis(di-2-thienylphosphine). M.p. 228° (thermoanalysis). $[\alpha]_D^{20} = -158.5$ (c=1, CHCl₃).

EXAMPLE 3

The following compounds were prepared in an analogous manner to Example 1:

(RS)-(6,6'-Dimethoxybiphenyl-2,2'-diyl)bis(di-3-furylphosphine oxide). M.p. 226°-227°.

(RS)-(6,6'-Dimethoxybiphenyl-2,2'-diyl)bis(di-3-furylphosphine).

(R)-(6,6'-Dimethoxybiphenyl-2,2'-diyl)bis(di-3-furylphosphine oxide). M.p. 230°-233°; $[\alpha]_D^{20} = +90.3$ (c=1, CHCl₃).

(R)-(6,6'-Dimethoxybiphenyl-2,2'-diyl)bis(di-3-furylphosphine). M.p. 128°-129°; $[\alpha]_D^{20} = +41.3$ (c=1, CHCl₃).

(S)-(6,6'-Dimethoxybiphenyl-2,2'-diyl)bis(di-3-furylphosphine oxide). $[\alpha]_D^{20} = -87$ (c=1, CHCl₃).

(S)-(6,6'-Dimethoxybiphenyl-2,2'-diyl)bis(di-3-furylphosphine). M.p. 135°; $[\alpha]_D^{20} = -41.3$ (c=1, CHCl₃).

EXAMPLE 4

0.6677 g (1.1 mmol) of (RS)-(6,6'-dimethylbiphenyl-2,2'-diyl)bis(di-2-thienylphosphine oxide), 1.49 g (11 mmol) of HSiCl₃ and 0.445 g (4.4 mmol) of triethylamine in 15 ml of xylene were placed under argon in a 1 l sulphonation flask provided with a condenser, thermometer, stirrer and headpiece for inert gas treatment and stirred under reflux for 4 hour. The clear solution obtained was treated cautiously with 5 ml of 30% NaOH solution, whereby the reaction temperature rose to ∼50°. The organic phase was separated and washed in succession with 5 ml of 30% NaOH solution and 10 ml of H₂O and dried over Na₂SO₄. After evaporation there was obtained a white powder which was washed with pentane and dried at ∼10 Pa. There was obtained 0.44 g of (RS)-(6,6'-dimethylbiphenyl-2,2'-diyl)bis(di-2-thienylphosphine). M.p. 177°-178°.

The (RS)-(6,6'-dimethylbiphenyl-2,2'-diyl)bis(di-2-thienylphosphine oxide) used as the starting material was prepared as follows:

a) 20 g (46.07 mmol) of (RS)-2,2'-diiodo-6,6'-dimethylbiphenyl, 23.72 g (101.3 mmol) of diphenyl phosphite, 12 g (119 mmol) of triethylamine and 2.62 g (2.26 mmol) of Pd(PPh₃)₄ were heated at 100° for 20 hours in a Schlenk tube while stirring. Thereafter, the reaction mixture was concentrated on a rotary evaporator, the residue was dissolved in CH₂Cl₂ and treated with NaOH solution. The organic phase was washed with water and dried over Na₂SO₄. The residue obtained after concentration of the organic phase was recrystallized from methanol. There were obtained 21.1 g of (RS)-(6,6'-dimethylbiphenyl-2,2'-diyl)bis(phosphonic acid diphenyl ester) as a pale beige powder.

b) 2.48 g (0.102 mol) of Mg turnings were covered with 10 ml of tetrahydrofuran under argon in a 1 l sulphonation flask provided with a condenser, thermometer, stirrer and headpiece for inert gas treatment and treated slowly while stirring with a solution of 15.13 g (92.8 mmol) of 2-bromothiophene in 20 ml of tetrahydrofuran, whereby the reaction temperature was held between 40° and 50°. The Grignard solution was diluted with 50 ml of tetrahydrofuran, transferred into a dropping funnel and added dropwise to a solution of 10 g (15.46 mmol) of (RS)-(6,6'-dimethylbiphenyl-2,2'-diyl)-bis(phosphonic acid diphenyl ester) in 60 ml of tetrahydrofuran. After 16 hours at 60° the suspension obtained was filtered and the filtrate was hydrolyzed with aqueous NH₄Cl solution. The aqueous phase was separated and the organic phase was washed in succession with sat. sodium hydroxide solution and sat. NaCl solution. After drying over Na₂SO₄ and evaporation the crude product was recrystallized from CH₂Cl₂/EtOH (1/1). There were obtained 5.63 g of (RS)-(6,6'-dimethylbiphenyl-2,2'-diyl)bis(di-2-thienylphosphine oxide) as an almost white crystalline powder.

EXAMPLE 5

The following compounds were prepared in an analogous manner to Example 4:

(RS)-(6,6'-Dimethylbiphenyl-2,2'-diyl)bis(di-2-furylphosphine oxide).

¹H-NMR (250 MHz, CDCl₃): 7.60-7.26 (m, 6 aromat. and 4 heteroaromat. H), 6.95, 6.90, 6.41, 6.30 (4m, in each case 2 heteroaromat. H), 1.87 (s, 2 aromat. CH₃).

(RS)-(6,6'-Dimethylbiphenyl-2,2'-diyl)bis(di-2-furylphosphine).

IR (KBr): 1546 (Ar), 788 (1,2,3-trisubst. benzene).
¹H-NMR (250 MHz, CDCl₃): 7.71-7.10 (m, 6 aromat. and 4 heteroaromat. H); 6.67, 6.41, 6.33, 6.27 (4m, in each case 2 heteroaromat. H): 1.51 (s, 2 aromat. CH₃).
MS: 345 (100, M+-P(C₄H₃O)₂).

EXAMPLE 6

The following compounds were prepared in an analogous manner to Example 4b):

(R)-(6,6'-Dimethylbiphenyl-2,2'-diyl)bis(di-2-thienylphosphine). M.p. 152°-154°; $[\alpha]_D^{20} = +163$ (c=1, CHCl₃).

(S)-(6,6'-Dimethylbiphenyl-2,2'-diyl)bis(di-2-thienylphosphine). M.p. 153°-154°; $[\alpha]_D^{20} = -161.6$ (c=1, CHCl$_3$).

The (R)- or (S)-(6,6'-dimethylbiphenyl-2,2'-diyl)bis(di-2-thienylphosphine oxide) used as the respective starting material was prepared as follows:

a) 5.46 g (9.0 mmol) of (RS)-(6,6'-dimethylbiphenyl-2,2'-diyl)bis(di-2-thienylphosphine oxide) [prepared in accordance with Example 4] were dissolved in 75 ml of CH$_2$Cl$_2$ at 40° in a 250 ml round flask and treated with a solution of 3.22 g (9.0 mmol) of (−)-0,0'-dibenzoyl-L-tartaric acid in 55 ml of ethyl acetate. After stirring at 0° for 2 hours the precipitated solid was filtered off, washed twice with 10 ml of ethyl acetate each time, dissolved in about 30 ml of CH$_2$Cl$_2$ and treated with 50 ml of a 1N NaOH solution. The organic phase was washed twice with water and subsequently dried over Na$_2$SO$_4$. After concentrating the solution and drying the residue at ~10 Pa there were obtained 1.13 g of (S)-(6,6'-dimethylbiphenyl-2,2'-diyl)bis(di-2-thienylphosphine) as a white crystalline powder. $[\alpha]_D^{20} = +42.66$ (c=1, CHCl$_3$).

b) The filtrate obtained from a) was treated with NaOH analogously as described there. There were obtained 3.9 g (6.43 mmol) of a white powder which was dissolved in 25 ml of CH$_2$Cl$_2$ at 40° and reacted with a solution of 2.3 g (6.43 mmol) of (+)-0,0'-dibenzoyl-D-tartaric acid in 15 ml of ethyl acetate. The clear solution obtained was cooled to 0° and treated as described under a). There were obtained 1.89 g of (R)-(6,6'-dimethylbiphenyl-2,2'-diyl)bis(di-2-thienylphosphine). $[\alpha]_D^{20} = -41.75$ (c=1, CHCl$_3$).

EXAMPLE 7

The following compounds were prepared in an analogous manner to Examples 4 and 5:

(S)-(6,6'-Dimethylbiphenyl-2,2'-diyl)bis(di-2-furylphosphine oxide).
$[\alpha]_D^{20} = +64.7$ (c=1, CHCl$_3$).

(S)-(6,6'-Dimethylbiphenyl-2,2'-diyl)bis(di-2-furylphosphine). M.p. 145°-146°; $[\alpha]_D^{20} = +88.6$ (c=1, CHCl$_3$).

(R)-(6,6'-Dimethylbiphenyl-2,2'-diyl)bis(di-2-furylphosphine oxide). $[\alpha]_D^{20} = -64.9$ (c=1, CHCl$_3$).

(R)-(6,6'-Dimethylbiphenyl-2,2'-diyl)bis(di-2-furylphosphine). M.p. 146°-147°; $[\alpha]_D^{20} = -88.8$ (c=1, CHCl$_3$).

EXAMPLE 8 a) A solution of 3.35 g (25.0 mmol) of benzothiophene in 14 ml of THF was allowed to flow via a canula within a few minutes into 14 ml of 1.6N butyllithium solution in hexane (19.6 mmol) at −78°, whereby the temperature rose to −45°. The resulting white suspension was left to warm to 0°, cooled to −15°, stirred at this temperature for a further 20 minutes and then again cooled to −78°. 6.0 g (23.2 mmol) of magnesium dibromide dietherate (MgBr$_2$. Et$_2$O) were introduced into the suspension and the mixture was left to warm to RT. The resulting solution was diluted with 20 ml of THF and allowed to flow via a canula at −78° on to 0.90 g (2.00 mmol) of (R)-(6,6'-dimethoxybiphenyl-2,2'-diyl)bis(phosphonic acid dichloride). Subsequently, the mixture was left to warm to RT and was again diluted with 20 ml of THF. The yellow-brown solution was treated with saturated NH$_4$Cl solution and ethyl acetate, the phases were separated and the organic phase was washed with water and saturated NaCl solution, dried over MgSO$_4$, filtered and evaporated. The residue was dissolved in the minimum amount of CH$_2$Cl$_2$ and chromatographed on 50 g of silica gel (hexane/ethyl acetate 1:1 and CH$_2$Cl$_2$/ethyl acetate 2:8), whereby (R)-(6,6'-dimethoxybiphenyl-2,2'-diyl)bis(dibenzo[b]thiophen-2-yl)-phosphine oxide was obtained as a beige powder. Recrystallization from CH$_2$Cl$_2$/ethyl acetate yielded 1.20 g (72%) of beige powder; m.p. 313°-315°; $[\alpha]_D^{20} = +132.9$ (c=1.0, CHCl$_3$).

The following compounds can also be prepared in an analogous manner to the foregoing:

(RS)-(6,6'-Dimethoxybiphenyl-2,2'-diyl)bis(dibenzo[b]thiophen-2-yl)phosphine oxide, m.p. 293°-295° (thermoanalysis 292.9°), (S)-(6,6'-dimethoxybiphenyl-2,2'-diyl)bis(dibenzo[b]thiophen-2-yl)phosphine oxide, m.p. 312°-316°; $[\alpha]_D^{20} = -132.9$ (c=1, CHCl$_3$).

b) The phosphine oxides obtained according to a) above were reduced according to example 1b) to the following compounds:

(R)-(6,6'-Dimethoxybiphenyl-2,2'-diyl)bis(dibenzo[b]thiophen-2-yl)-phosphine, m.p. 252°-254°; $[\alpha]_D^{20} = +94.9$ (c=1, CHCl$_3$), (S)-(6,6'-dimethoxybiphenyl-2,2'-diyl)bis(dibenzo[b]thiophen-2-yl)-phosphine, m.p. 252°-253°; $[\alpha]_D^{20} = -93.4$ (c=1, CHCl$_3$), (RS)-(6,6'-dimethoxybiphenyl-2,2'-diyl)bis(dibenzo[b]thiophen-2-yl)-phosphine.

The (R)-(6,6'-dimethoxybiphenyl-2,2'-diyl)bis(phosphonic acid dichloride) used as the starting material in a) was prepared as follows:

A solution of 4.86 g (10.0 mmol) of (R)-(6,6'-dimethoxybiphenyl-2,2'-diyl)bis(phosphonic acid diethyl ester) [m.p. 125°-126°; $[\alpha]_D^{20} = +32.7$ (c=1, CHCl$_3$); prepared in analogy to the preparation of the corresponding diphenyl ester in accordance with Example 1], 10 ml (16.33 g, 137 mmol) of thionyl chloride and 1.0 ml of dry dimethylformamide was boiled at reflux for 6 hours under argon. The excess thionyl chloride was subsequently distilled off and the residue was dried in a high vacuum (~10 Pa) at 100° for 1 hour. The viscous oil obtained was taken up in 30 ml of CH$_2$Cl$_2$. After filtering off a small amount of insoluble material the filtrate was treated with 40 ml of ether, whereby a white powder separated. Filtration, washing with ether and drying in a high vacuum (~10 Pa) yielded 3.10 g of (R)-(6,6'-dimethoxybiphenyl-2,2'-diyl)bis(phosphonic acid dichloride) of m.p. 172°-178°; $[\alpha]_D^{20} = +51.3$ (c=1, CHCl$_3$).

The following compounds were prepared in an analogous manner to the foregoing:

(S)-(6,6'-Dimethoxybiphenyl-2,2'-diyl)bis(phosphonic acid dichloride), m.p. 172°-178°; $[\alpha]_D^{20} = -50.2$ (c=1, CHCl$_3$), (RS)-(6,6'-dimethoxybiphenyl-2,2'-diyl)bis(phosphonic acid dichloride, m.p. 195°-198°.

EXAMPLE 9

The following compounds can also be prepared in an analogous manner to Example 8:

(R)-(6,6'-Dimethoxybiphenyl-2,2'-diyl)bis(dibenzo[b]furan-2-yl)phosphine oxide, m.p. 288°-292°; $[\alpha]_D^{20} = +82.3$ (c=1, CHCl$_3$), (R)-(6,6'-dimethoxybiphenyl-2,2'-diyl)bis(dibenzo[b]furan-2-yl)phosphine, m.p. 239°-241°; $[\alpha]_D^{20} = +31.6$ (c=1, CHCl$_3$), (S)-(6,6'-dimethoxybiphenyl-2,2'-diyl)bis(dibenzo[b]furan-2-yl)phosphine oxide, m.p. 287°-289°; [α]$_D^{20}$= −80.8 (c=1, CHCl$_3$), (S)-(6,6'-dimethoxybiphenyl-2,2'-diyl)bis(dibenzo[b]furan-2-yl)phosphine, m.p. 239°-240°; [α]$_D^{20}$= −30.6 (c=1, CHCl$_3$), (RS)-(6,6'-dimethoxybiphenyl-2,2'-diyl)bis(dibenzo[b]furan-2-yl)phosphine oxide, (RS)-(6,6'-dimethoxybiphenyl-2,2'-diyl)bis(dibenzo[b]furan-2-yl)phosphine, (RS)-(6,6'-dimethoxybiphenyl-2,2'-diyl)bis[bis(5-methylfuran-2-yl)phosphine oxide, m.p. 201°-204°, (RS)-(6,6'-dimethoxybiphenyl-2,2'-diyl)bis[bis(5-methylfuran-2-yl)phosphine], m.p. 159°-160°, (R)-(6,6'-dimethoxybiphenyl-2,2'-diyl)bis[bis(5-methylfuran-2-yl)phosphine oxide], m.p. 231°-234°; [α]$_D^{20}$= −87.8 (c=1, CHCl$_3$), (R)-(6,6'-dimethoxybiphenyl-2,2'-diyl)bis[bis(5-methylfuran-2-yl)phosphine], m.p. 146°-150°; [α]$_D^{20}$= +20.6 (c=1, CHCl$_3$), (S)-(6,6'-dimethoxybiphenyl-2,2'-diyl)bis[bis(5-methylfuran-2-yl)phosphine oxide], m.p. 229°-233°; [α]$_D^{20}$= −72.4 (c=1, CHCl$_3$), (S)-(6,6'-dimethoxybiphenyl-2,2'-diyl)bis[bis(5-methylfuran-2-yl)phosphine], m.p. 146°-150°; [α]$_D^{20}$= −20.1 (c=1, CHCl$_3$), (RS)-(6,6'-dimethoxybiphenyl-2,2'-diyl)bis[bis(1-methylpyrrol-2-yl)phosphine oxide], m.p. 297°-299°, (RS)-(6,6'-dimethoxybiphenyl-2,2'-diyl)bis[bis(1-methylpyrrol-2-yl)phosphine], m.p. 162°-166°, (R)-(6,6'-dimethoxybiphenyl-2,2'-diyl)bis[bis(1-methylpyrrol-2-yl)phosphine oxide], m.p. 298°-302°; [α]$_D^{20}$= +12.4 (c=1, CHCl$_3$), (R)-(6,6'-dimethoxybiphenyl-2,2'-diyl)bis[bis(1-methylpyrrol-2-yl)phosphine], (S)-(6,6'-dimethoxybiphenyl-2,2'-diyl)bis[bis(1-methylpyrrol-2-yl)phosphine oxide], (S)-(6,6'-dimethoxybiphenyl-2,2'-diyl)bis[bis(1-methylpyrrol-2-yl)phosphine].

EXAMPLE 10 a) 9.7 mg (0.02 mmol) of dichloro-bis-(1,5-cyclooctadiene)dirhodium and 22.7 mg (0.04 mmol) of (S)-(6,6'-dimethylbiphenyl-2,2'-diyl)bis(di-2-thienylphosphine) were dissolved in 50 ml of toluene at room temperature while stirring in a 50 ml measuring flask in a glove box (O$_2$ content <1 ppm). An orange-red clear catalyst solution formed within 10 minutes.

b) A 500 ml autoclave was charged in a glove box (O$_2$ content <1 ppm) with 16.11 g (78.85 mmol) of (E)-3-(4-tert.butylphenyl)-2-methylprop-2-en-1-ol, 145 ml of toluene and 5 ml of catalyst solution (in accordance with a)). This mixture was hydrogenated at 100°, a constant pressure of 60 bar H$_2$ and while stirring intensively. The conversion was >99% after 22 hours. The pale yellow hydrogenation solution was rinsed from the autoclave and evaporated on a rotary evaporator at 60°/17 mbar. The residue was distilled at 140°/0.01 mbar. There were obtained 16.0 g (99.0%) of (R)-3-(4-tert.butylphenyl)-2-methylpropan-1-ol as a colourless oil with an enantiomeric purity of 91.3% e.e.

The hydrogenation was carried out in an analogous manner to the foregoing using a catalyst solution prepared from (R)-(6,6'-dimethylbiphenyl-2,2'-diyl)bis(di-2-thienylphosphine). In this case the enantiomeric purity was 90.2% e.e.

EXAMPLE 11 a) 11.2 mg (0.013 mmol) of tetra-μ-trifluoroacetatobis(1,5-cyclooctadiene)diruthenium(II) and 13.2 mg (0.026 mmol) of (S)-(6,6'-dimethylbiphenyl-2,2'-diyl)bis(di-2-furylphosphine) were dissolved in 100 ml of methanol while stirring at room temperature in a 100 ml measuring flask in a glove box (O$_2$ content <1 ppm). An orange-red clear catalyst solution formed within 16 hours.

b) A 500 ml autoclave was charged in a glove box (O$_2$ content <1 ppm) with 24.0 g (155.6 mmol) of (E)-3,7-dimethylocta-2,6-dien-1-ol, 22 ml of methanol and 100 ml of catalyst solution. This mixture was hydrogenated at 20°, a constant pressure of 60 bar H$_2$ and while stirring intensively. The conversion was 100% after 48 hours. The pale yellow hydrogenation solution was rinsed from the autoclave and evaporated on a rotary evaporator at 60°/17 mbar. The residue was distilled at 65%/0.01 mbar. There were obtained 23.8 g of (R)-3,7-dimethyloct-6-en-1-ol as a colourless oil with an enantiomeric purity of 98.4% e.e.

EXAMPLE 12

(E)-3,7-Dimethylocta-2,6-dien-1-ol was hydrogenated in an analogous manner to Example 9 in the presence of a catalyst solution prepared from (S)-(6,6'-dimethylbiphenyl)bis(di-2-thienylphosphine). In this case the enantiomeric purity was 98.8% e.e.

We claim:

1. Racemic and optically active phosphorus compounds of the general formula

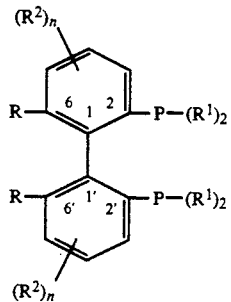

I wherein R signifies lower alkyl, lower alkoxy or a protected hydroxy group, R$^1$ signifies a five-membered heteroaromatic ring, R$^2$ stands for lower alkyl or lower alkoxy and n represents the number 0, 1 or 2.

2. Phosphorus compounds in accordance with claim 1 in the (R) or (S) form.

3. Phosphorus compounds in accordance with claim 1 or 2, wherein n stands for the number 0.

4. Phosphorus compounds in accordance with claim 3, wherein R$^1$ signifies 2-furyl, 3-furyl, 2-thienyl, 5-methylfuran-2-yl, 2-benzo[b]furanyl, dibenzo[b]thiophen-2-yl or 1-methylpyrrol-2-yl.

5. The phosphorate compound of claim 4 wherein said compound is (RS)-, (R)- or (S)-(6,6'-dimethoxybiphenyl-2,2'-diyl)bis(di-2-furylphosphine).

6. The phosphorate compound of claim 4 wherein said compound is (RS)-, (R)- or (S)-(6,6'-dimethoxybiphenyl-2,2'-diyl)bis(di-2-thienylphosphine).

7. The phosphorate compound of claim 4 wherein said compound is (RS)-, (R)- or (S)-(6,6'-dimethylbiphenyl-2,2'-diyl)bis(di-2-furylphosphine).

8. The phosphorate compound of claim 4 wherein said compound is (RS)-, (R)-, or (S)-(6,6'-dimethylbiphenyl-2,2'-diyl)bis(di-2-thienylphosphine).

* * * * *